United States Patent
Hiepe et al.

[11] Patent Number: 5,945,105
[45] Date of Patent: Aug. 31, 1999

[54] PEPTIDES OF THE ANTIGEN SM-D AND THEIR USE, IN PARTICULAR FOR THE DIAGNOSTICS OF SYSTEMIC LUPUS ERYTHEMATOSUS (SLE)

[75] Inventors: Falk Hiepe; Gabriele Riemekasten; Jeannette Marell; Gerd-Rüdiger Burmester, all of Berlin, Germany

[73] Assignee: Imtec Immundiagnostika GmbH

[21] Appl. No.: 08/733,982

[22] Filed: Oct. 18, 1996

[30] Foreign Application Priority Data

Oct. 19, 1995 [DE] Germany .......................... 195 38 968
May 14, 1996 [DE] Germany .......................... 196 19 418

[51] Int. Cl.⁶ .................................................. A61K 38/00
[52] U.S. Cl. ......................... 424/185.1; 514/12; 530/324
[58] Field of Search ............................. 514/12; 530/324; 424/185.1

[56] References Cited

U.S. PATENT DOCUMENTS 5,407,833  4/1995  Van Regenmortel ................... 436/508

OTHER PUBLICATIONS

Wraith et al., Cell, vol. 59: 247–255, Dec. 1989.

Tisch et al., Proc. Natl. Acad. Sci. USA, vol. 91: 437–438, Jan. 1994.

*Primary Examiner*—Christina Y. Chan
*Assistant Examiner*—Patrick J. Nolan
*Attorney, Agent, or Firm*—Horst M. Kasper

[57] ABSTRACT

Peptides of the antigen Sm-D and their use, in particular for the diagnostics of the SLE. The invention relates to peptides of the antigen Sm-D, comprised of 35 to 45 amino acids, which form a conformation epitope and which are capable of binding autoantibodies, such as they occur in connection with systemic lupus erythematosus (SLE). Particularly preferred is the peptide of 37 amino acids with the structure V E P K V K S K K R E A V A G R G R G R G R G R G R-GRGRGGPRR (SEQ ID NO:3) and its mutants and variants, respectively.

9 Claims, 6 Drawing Sheets

PEPTIDES OF THE ANTIGEN SM-D AND THEIR USE, IN PARTICULAR FOR THE DIAGNOSTICS OF SYSTEMIC LUPUS ERYTHEMATOSUS (SLE)

The present application claims priority under 35 U.S.C. 119(a)–(d) to foreign applications DE 195 38968.9, filed Oct. 19, 1995 and DE 196 19418.0, filed May 14, 1996.

BACKGROUND OF THE INVENTION

1. Field of the Invention

The invention relates to the peptides of the antigen Sm-D, which are recognized by antibodies in biological fluids, in particular of antibodies which are present in the body fluids of patients which suffer from systemic lupus erythematosus (SLE).

Furthermore, the invention relates to the use of these peptides and their sequential products for the diagnostics of SLE in vitro, as well as their use as a vaccine for the generation of tolerance mechanisms and for the preparation of immunogenic and antigenic compositions and of test kits.

In addition, the invention concerns antibodies which are induced in vivo by these peptides as well as a method for the determination of anti-Sm-D antibodies in biological fluids.

2. Brief Description of the Background of the Invention Including Prior Art

It is known that many autoantigens are positioned in a close spatial relationship. For example, the Sm and the various ribonucleoproteins RNP form a ribonucleoprotein complex, which is present in the core of eukariotic cells (snRNP). Anti Sm antibodies recognize various proteins of the snRNP complex, which are designated as B', B, D, E, F, and G. This complex probably plays a central role in the splicing of the pre-mRNA, wherein the Sm-D protein represents an important regulation protein, in that it is to regulate the binding of various ribonucleic acids.

It is ultimately undetermined which mechanisms lead to the formation of autoantibodies. It is noticeable that particularly important regulatory centers for the cell cycle are the goal of the autoantibodies of the SLE and of syndromes related to SLE. Upon the generation of the autoimmune diseases, particularly important regions are in general to be recognized by autoantigens and are to interfere with the physiological functioning of the particularly important regions of the autoantigens.

Bloom and coworkers could prove in connection with investigations of hybridoma cell lines, produced by means of hybridoma technique, that anti-Sm antibodies can also recognize deoxyribonucleic acid DNA (D. D. Bloom et al, Journal Immunol. 1993; 150 (4): 1579–1590). The authors concluded from this that the Sm-D protein by itself does not act as antigen for the formation of anti-Sm antibodies. Rather, it is assumed that both the Sm-D autoantigen and the deoxyribonucleic acid DNA, possibly as a complex, form the autoimmune agent. No binding capability of the Sm-D protein with the deoxyribonucleic acid DNA could be determined up to now. The physiological and pathophysiological importance of the Sm/deoxyribonucleic acid DNA complex is not known up to now.

Lebrun and coworkers carried out immunization tests at certain breeds of mice with deoxyribonucleic acid DNA, wherein they coupled the deoxyribonucleic acid DNA with a fusion protein, rich in arginine, and they could thereby generate a lupus nephritis (P. Lebrun et al, Lupus 1994; 3: 47–53). They also concluded that certain proteins, binding to the deoxyribonucleic acid DNA, are necessary in order to generate an autoimmune reaction.

In addition to the antibodies (Ad) against native or double-stranded deoxyribonucleic acid (dsDNA), anti-Sm antibodies are deemed to be a diagnostic marker for the systemic lupus erythematosus (SLE). In addition, a pathogenic role is attributed to the anti-Sm antibodies in the generation of damages to organs. The proof of the anti-Sm antibodies succeeds in Europe, contrary to the anti-ds-DNA antibodies, only in case of relatively few patients, whereas in the United States it can be determined in one third of the patients with SLE. The cause of this is considered to be a different ethnic composition of the population (N. Abuaf et al. Eur. J. Clin. Invest. 1990; 20: 354–359).

There are several methods of determining the presence of anti-Sm antibodies.

The immuno diffusion and countercurrent electrophoresis are relatively specific methods for a detection of anti-Sm antibodies, however, these methods are relatively insensitive and, in addition, time-consuming and expensive.

Anti-Sm antibodies can be detected by way of immuno blotting depending on the used antigen substrate in about 30% of the SLE patients also in Europe (G. Riemekasten and F. Hiepe, Zeitschrift ärztlicher Fortbildung, 1992; 86: 217–222). It is possible based on this method to characterize the anti-Sm antibodies in a better way. Anti-Sm antibody-positive patients react amongst others with the B'B proteins as well as with the proteins D, E, F, and G of a small nucleic ribonucleoprotein complex (snRNP). While anti-B'B antibodies are not so specific for the SLE, the antibodies in particular against the D protein are deemed to be SLE specific.

This immuno blotting method is however associated with the disadvantage that it requires a substantial time expenditure and is expensive. In addition, a lot of experience is necessary in the connection with the evaluation.

Therefore, commercially available ELISA techniques are employed in many laboratories for detecting the presence of Sm antibodies, which ELISA techniques are characterized by a high sensitivity and by a relatively simple production practicability at a high sample throughput. These tests are for example performed on the basis of Sm purified from thymus extracts as a solid-phase antigen (printed patent document WO 90/10229) and of recombinant produced Sm antigen (L. A. Rokeach et al., Clinical Immunology and Immunopathology 1992; 65(3): 315–324). Rokeach and coworkers could isolate for the first time the cDNA of the Sm-D protein and could show that it codes a protein consisting of 119 amino acids.

Thus, the foundations were created for the generation of the ELISAs on the basis of synthesized peptides, cf. European printed patent document EP 0,295,719, wherein the application of cloned Sm-D was described for the diagnostics of the SLE.

A multitude of these, in part also commercially available tests are however relatively unstable, time-consuming and, based on false positive results due to cross reactions, less specific (printed patent document WO 90/10229).

In order to determine the main epitopes of the Sm-D protein, James and coworkers have subdivided the complete SmD protein into overlapping octapeptides and have investigated the reactivities in the ELISA relative to 15 SLE sera (James et al., Clin. exp. Immunol. 1994; 98: 419–426). Five epitopes were found, the main epitopes were also at the C-terminal end as well as epitopes of the amino acids 37–53, of the amino acids 69–76, and of the amino acids 5–12.

Barakat and coworkers found three regions of the SmD protein (first region amino acids 1 through 20, second region amino acids 44 through 67, and third region amino acids 97 through 119) with which anti-SmD antibody-positive sera reacted which had been previously detected in immuno blotting (Barakat et al., Clin. exp. Immunol. 1990; 81: 256–262). 67% of the overall 18 anti-SmD antibody-positive sera reacted with the peptide 1–20, 89% with the peptide 44–67, and only 33% with the peptide 97–119. 165 of the SLE sera were tested relative to their reactivity in the ELISA with the peptides 1–20, 44–67, and 97–119, wherein positive reactions occurred in 59%, 37%, and 1%. Sabbatini and coworkers found positive reactions against the region 95–119 in 25% of the 48 SLE sera in the ELISA (A. Sabbatini et al., J. Rheumatol. 1993; 20: 1679–1683).

Short-chain peptides were used in connection with all these investigations and the number of the positive results of the SLE sera varied for the C-terminal end between 1% and 33% in the ELISA. Thus, these synthetically produced peptides are not associated with a substantial advantage relative to the commercially available tests. Only linear epitopes can be captured with this epitope mapping. The reactivity in connection with autoimmune diseases, however, is directed against intact autoantigens (E. M. Tan, J. Exp. Med. 1994; 179: 1083–1086).

In connection with a possible use of the complete SM-D antigen, there exists the danger that important epitopes are no longer accessible to the antibodies based on the secondary and tertiary structure. In addition, a new conformation can be generated by binding of parts of the Sm-D antigen to other autoantigens, preferably DNA.

A proof of a reactivity of the anti-La antibody, which is directed against a conformation epitope, could be furnished by way of peptide chains of the La protein of different lengths as a solid-phase antigen in the ELISA by Rischmueller and coworkers (M. Rischmueller et al., Clin. exp. Immunol. 1995; 101: 39–44).

The peptides of the Sm-D antigen and their use for the diagnostics of the SLE are described in the printed patent document WO 91/18920. These known peptides, wherein the amino acids are mainly directly N terminal, exhibit however only a low frequency of positive reactions (approximately 30% positive reactions).

SUMMARY OF THE INVENTION

1. Purposes of the Invention

Therefore, it was an object of the present invention to furnish specific peptides of the antigen Sm-D, wherein these peptides and their sequential products are particularly well suitable for the diagnosis of SLE.

Furthermore, it was an object of the present invention to develop a simple, quickly performable, and safe test for the diagnosis of the SLE based on these peptides, i.e. to lower the percentage of true-positive to false-positive results.

In addition, the object comprises to form antibodies and anti-idiotype antibodies or to bind them, wherein the antibodies and anti-idiotype antibodies correspond in their specificity to the autoantibodies of SLE patients.

a) PKVKSKKREAVAGRGRGRGRGRGRGRGR GGPRR, SEQ ID No. 1, b) EPKVKSKKREAVAGRGRGRGRGRGRGRGR GGPRR, SEQ ID No. 2, c) VEPXVKSKKREAVAGRGRGRGRGRGRGR GRGGPRR, SEQ ID No. 3, d) DVEPKVKSKKREAVAGRGRGRGRGRGRGR GRGGPRR, SEQ ID No. 4, e) VDVEPKVKSKKREAVAGRGRGRGRGRGRGR GRGRGGPRR, SEQ ID No. 5, f) RVDVEPKVKSKXREAVAGRGRGRGRGRGRG RGRGRGGPRR, SEQ ID No. 6, g) IRVDVEPKVKSKKREAVAGRGRGRGRGRGR GRGRGGPRR, SEQ ID No. 7, h) TIRVDVEPKVKSKKREAVAGRGRGRGRGRGR GRGRGGPRR, SEQ ID No. 8, i) DTIRVDVEPKVKSKKREAVAGRGRGRGRGRGRG RGRGRGGPRR, SEQ ID No. 9, j) LDTIRVDVEPKVKSKKREAVAGRGRGRGRGR GRGRGRGGPRR, SEQ ID No. 10, and k) PLDTIRVDVEPKVKSKKREAVAGRGRGRGRG RGRGRGRGGPRR, SEQ ID No. 11.

The present invention further comprises an antigen composition and an immunogenic composition comprising a peptide of the antigen Sm-D as set forth above.

DESCRIPTION OF THE INVENTION AND PREFERRED EMBODIMENT

It was surprising that such peptides, which form a conformation epitope and which are capable of binding autoantibodies, as they occur in the systemic lupus erythematosus (SLE), are found in the peptides of the protein Sm-D with a sequence of 35 to 45 amino acids.

Preferably, the peptides concerned are:

a) PKVKSKKREAVAGRGRGRGRGRGRGRGR-GRGGPRR (SEQ ID NO:1)

b) EPKVKSKKREAVAGRGRGRGRGRGRGRGR-GRGRGGPRR (SEQ ID NO:2)

c) VEPKVKSKKREAVAGRGRGRGRGRGRGRGR-GRGRGGPRR (SEQ ID NO:3)

d) DVEPKVKSKKREAVAGRGRGRGRGRGRGR-GRGRGRGGPRR (SEQ ID NO:4)

e) VDVEPKVKSKKREAVAGRGRGRGRGR-GRGRGRGGPRR (SEQ ID NO:5)

f) RVDVEPKVKSKKREAVAGRGRGRGRGR-GRGRGRGRGGPRR (SEQ ID NO:6)

g) IRVDVEPKVKSKKREAVAGRGRGRGR-GRGRGRGRGGPRR (SEQ ID NO:7)

h) TIRVDVEPKVKSKKREAVAGRGRGR-GRGRGRGRGRGGPRR (SEQ ID NO:8)

i) DTIRVDVEPKVKSKKREAVAGRGRGR-GRGRGRGRGRGGPRR (SEQ ID NO:9)

j) LDTIRVDVEPKVKSKKREAVAGRGR-GRGRGRGRGRGRGGPRR (SEQ ID NO:10)

k) PLDTIRVDVEPKVKSKKREAVAGRGR-GRGRGRGRGRGRGGPRR (SEQ ID NO:11).

In particular preferred is the peptide of 37 amino acids with the structure

VEPKVKSKKREAVAGRGRGRGRGRGRGRGRGGPRR, (SEQ ID NO:3)

and its mutants and variants, respectively, namely with a structure which is changed at one or several arbitrary positions by exchange of amino acids or, respectively, with a structure which is changed at one or several arbitrary positions by elimination of amino acids.

The synthesis of the peptides is performed according to the in principle conventional methods (E. Atheron and C. Sheppard, In Solid Phase Synthesis—A Practical Approach, IRL Press at Oxford University Press, 1989).

The specificity test and the activity test of these peptides is performed by way of "Enzyme-linked immunosorbent assay" (ELISA).

Antibodies according to the present invention, which are directed against conformation epitope of the Sm-D antigen, are characterized in that they are capable of recognizing one or several of the invention peptides of the antigen Sm-D, in particular the above recited peptides a) through k) and their mutants and variants, respectively. Their production is performed according to the in principle conventional method by —immunization of mice or immunization of spleen cells in vitro with the invention peptides, —isolation of the spleen cells and fusioning with cancer cells to form hybridoma cells; selection of positive clones —isolation of the antibodies.

These antibodies are employed both in various immunological test systems, in different ELISA tests systems, in the flow-through cytometry, and in the Western Blot.

Anti-idiotype antibodies according to the invention, which are formed against antibodies, which are directed against conformation epitopes of the Sm-D antigen and which recognize the peptides according to the present invention, are characterized in that they recognize in a specific way the autoantibodies of the SLE in biological fluids. Their production is performed also according to methods, which are known in principle, by immunization with the corresponding autoantibodies.

Antigenic compositions contain according to the invention one or several of these peptides according to the invention, preferably the peptide VEPKVKSKKREAV-AGRGRGRGRGRGRGRGRGGPRR (SEQ ID NO:3) and their mutants and variants, respectively, and are characterized in that they react specifically with the autoantibodies, as they are present in biological fluids in the SLE, and that they are possible coupled to different carriers, such as polystyrene, chemically activated polystyrene, activated Sepharose [translator's remark: tradename, Pharmacia], celluloses, and similar agents, which can still further improve the antigenic properties.

Immunogenic compositions contain a peptide according to the invention or a compound of this peptide with a carrier molecule or with another autoantigen, preferably deoxyribonucleic acid DNA, preferred is the peptide VEPKVK-SKKREAVAGRGRGRGRGRGRGRGRGGPRR (SEQ ID NO:3) and its mutants and variants, respectively, and they induce the production of the antibodies, which are capable to recognize autoantigens of the SLE.

The method according to the invention for the determination of the anti-Sm-D antibodies in biological fluids is performed in that at least one of the peptides according to the invention, which is possibly coupled to a carrier material, or also an anti-idiotype antibody with the biological fluids, is brought into contact under conditions, which allow an antigen antibody reaction, and wherein the detection of the presence of this antigen antibody reaction is performed by physical methods or chemical methods.

According to the invention, a test kit is in addition made available for the determination of anti-Sm-D antibodies. This test kit is characterized in that it contains —at least one peptide according to the invention or a combination of this peptide with a carrier molecule, preferably the peptide VEPKVKSKKREAVAGR-GRGRGRGRGRGRGGPRR (SEQ ID NO:3) and its mutants and variants, respectively, or also an anti-idiotype antibody according to the present invention, which is bound adsorptively or covalent to a solid phase, —a buffer for the thinning of the biological liquid to be investigated, which contains non-ionic or ionic detergents or proteins, —a specific conjugate, comprising an antibody, which is directed against human immunoglobulin IgG, IgM, IgA or against several of these immunoglobulins, and an enzyme, —a buffer for the thinning of the conjugate, which buffer contains non-ionic detergents or ionic detergents or proteins, —a buffer for the washing (removal) of the non-bound immuno reactants, which contains non-ionic detergents or ionic detergents or proteins, —a substrate solution for detecting the presence of the enzyme reaction, and —a stop solution for interrupting the enzyme reaction.

The determinations of the course can be performed relatively simple and quickly with the development of this new test kit based on the peptides according to the present invention.

Anti-Sm antibodies can be detected at least as frequently as anti-dsDNA antibodies with the test according to the present invention, which contains a long peptide of the Sm-D with 35–45 amino acids at the solid phase. The titer of the antibodies correlate well with the disease activity of the SLE such that this test in addition to the symptoms of the disease allows a determination of the course and an evaluation of the success of the therapy. Thus, expensive tests can be replaced.

Surprisingly, the peptides according to the present invention show an unusually high frequency of positive reactions. For example, the positive reaction for the peptide VEPKVK-SKKREAVAGRGRGRGRGRGRGRGRGGPRR (SEQ ID NO:3) are higher than 67%, whereby analogously known peptides (positive reactions at about 30%) are clearly surpassed (compare FIG. 1).

The diagnosis of an SLE can be performed with high assurance based on the invention. The invention, however, is not only extremely well suited to the diagnosis of the SLE, but in addition also for a therapeutic control (monitoring) as well as for the production of medication against SLE.

In addition, the peptides according to the invention and their sequential products can be employed as a vaccine for the generation of tolerance mechanisms.

In the following the invention is illustrated by way of examples, which however are not to limit the invention to these examples.

EXAMPLE 1

In order to capture a conformation epitope, four different peptides of the Sm-D protein were synthesized.
1. Peptide 83–99 with the following sequence VEPKVK-SKKREAVAGRG (SEQ ID NO:12) 2. Peptide 95–119 with the following sequence VAGRGRGRGRGRGR-GRGRGRGGPRR (SEQ ID NO:13) 3. Peptide 105–119 with the following sequence GRGRGRGR-GRGGPRR (SEQ ID NO:14) 4. Peptide 83–119 with the following sequence VEPKVKSKKREAVAGRGR-GRGRGRGRGRGRGGPRR (SEQ ID NO:3).

The synthesis of these peptides was performed according to the method, which was described for the first time by Atherton (compare above). For the purification of these peptides, a 300×40 mm VYDAC TPB 1520 300A C18 reverse phase column was used. The flow rate amounted to 100 ml/min.

These peptides were tested in an ELISA.

Production of the ELISA

Coating of the Antigen (Peptide) to the Solid Phase of the ELISAs

Polystyrene plates (Nunc, Denmark) with in each case 96 wells were employed for the coating. The coating was performed with 10 μg/ml, wherein 50 μl were employed for each well. A 0.05 M carbonate buffer, pH 9.5, was used as a coating medium.

The coating occurred overnight at room temperature or 4° C. After a three-time washing with the washing buffer (PBS-Tween 0.1%, pH 7.2), the plates were either further used or were frozen at −20° C.

The plates were washed again three times prior to reuse after the freezing.

Application of Samples of 40 SLE Sera as well as 50 Sera of Healthy Test Persons Prior to the application of the sample, there was performed a preblocking of the plates with in each case 100 μl per well sample buffer (PBS-Tween, pH 7.2, in a ratio of 1:100 with dried milk) for one hour at room temperature. Without following up with a washing process, the application of the samples (thinning of the serum 1:100 in a sample buffers) was performed with in each case 50 μl per well over two hours at room temperature. In the following, the washing process was performed three times with the washing buffer.

Addition of the Conjugate

The incubation with POD-marked anti-human IgG was performed in a dilution of 1:1000 in sample buffers in each case of 50 μl per well over two hours at room temperature. In the following, washing occurred again three times with the washing buffer.

Coloration

The coloration of the antigen antibody reaction was performed with 10 ml citrate buffer, pH 5.0, 5 μl hydrogen-peroxide $H_2O_2$, and 5 mg orthophenylene diamine (OPD) in each case 50 μl per well over a time period of 1 to 3 minutes. The stopping was performed with 150 μl per well stopping solution (100 ml 1 M hydrosulfuric acid $H_2SO_4$, 0.36 mg sodium sulfite). The color intensity or the optical density (extinctions) were determined at 495 mm. The resulting color of the reaction is proportional to the number of the conjugated antibodies, as in the case in each other ELISA, which antibodies were bound at the test antibody. In most cases, the number of the bound conjugated antibodies is linear relative to the number of the antibodies bound to the antigen.

A standard serum was used for the generation of a calibration curve, which reacted particularly well in preperformed tests. The concentration of this standard serum in a dilution of 1:100 was defined as 10,000 units. This calibration curve was plotted to each plate, and each serum was determined twice.

The normal region (NR) was defined with: NR=average value of the normal sera plus the two-fold value of the stray region of the normal sera (n=106). The norm value according to this calculation was at a concentration of 223 units, calculated from a standard curve, for the test system according to the present invention.

Figure 1:
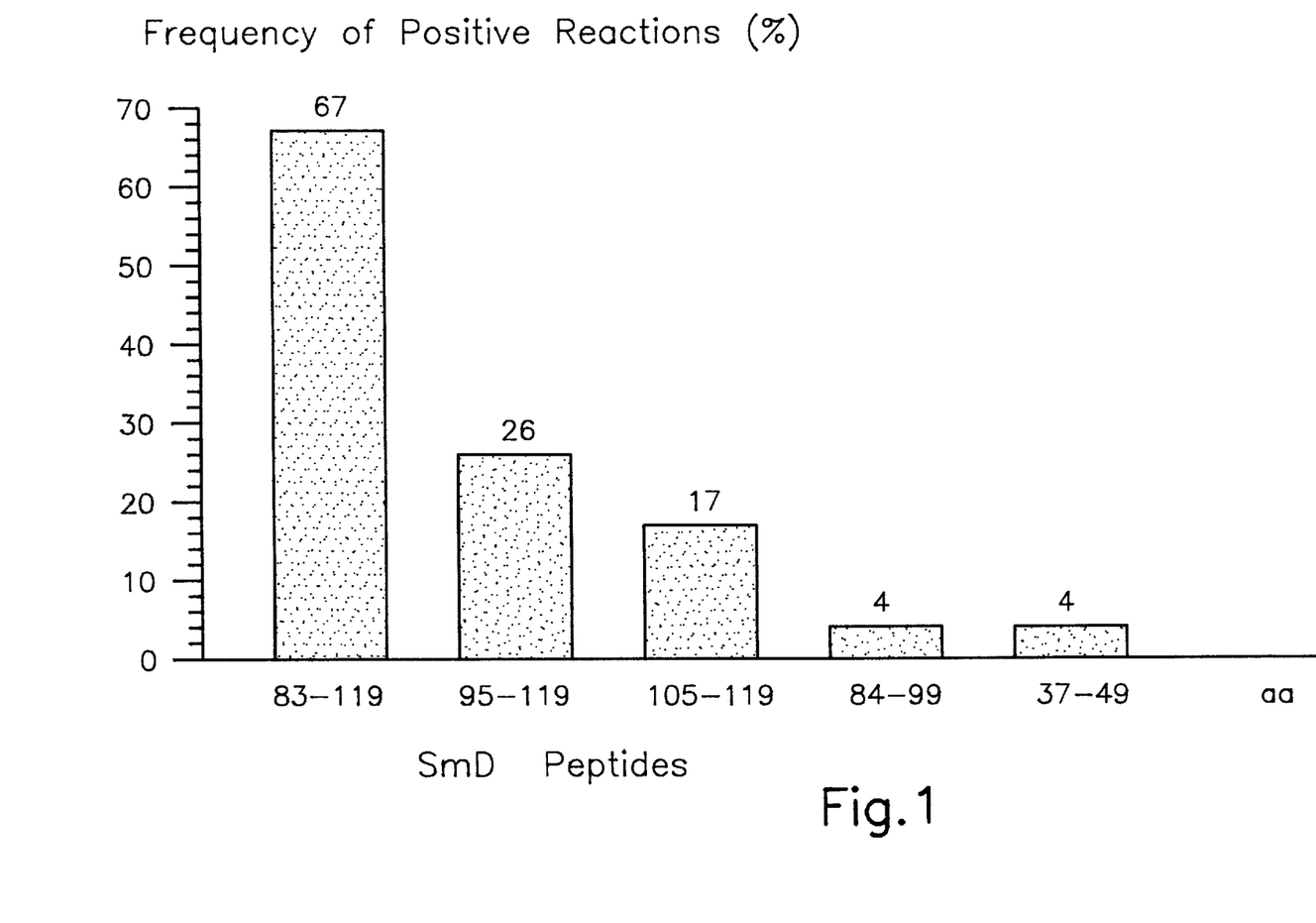
FIG. 1 is a block diagram showing the presence of anti-Sm antibodies while using different SmD peptides as test-phase antigen in the ELISA.

FIG. 1 shows the schematic representation of the peptides and their reactivity at the 40 SLE sera as well as at the 50 healthy test persons.

The limit relative to the normal region was determined from the average extinction of the 106 blood donors plus the two-fold value of the stray region. Employing the relatively short peptides 83–99 and 95–119, positive reactions were measured in the ELISA only in each case in 4% or, respectively 25% of the investigated sera. In contrast, if the peptide with the amino acid from 83–119 was employed as a solid-phase antigen, then a clear rise of the positive reactions to about 70% of all investigated SLE sera occurred (FIG. 1).

Surprisingly, it was shown that the use of longer peptides as solid-phase antigen in the ELISA brings clearly a qualitative improvement relative to the assays previously described.

EXAMPLE 2

Investigations Relative to the Specificity and Sensitivity of the ELISAs with the Peptide 83–119

A total of 176 SLE sera, 89 sera of HIV-infected patients, 25 MCTD sera, 28 sera of patients with a rheumatic arthritis, 15 sera with patients having Sjögren's syndrome, 20 sera with a progressive sclerodermia (PSS), 30 sera of patients with a Lyme disease, 20 Hepatitis B-positive patients, 25 sera with colitis ulcerosa, and 105 blood donors were tested.

Figure 2:
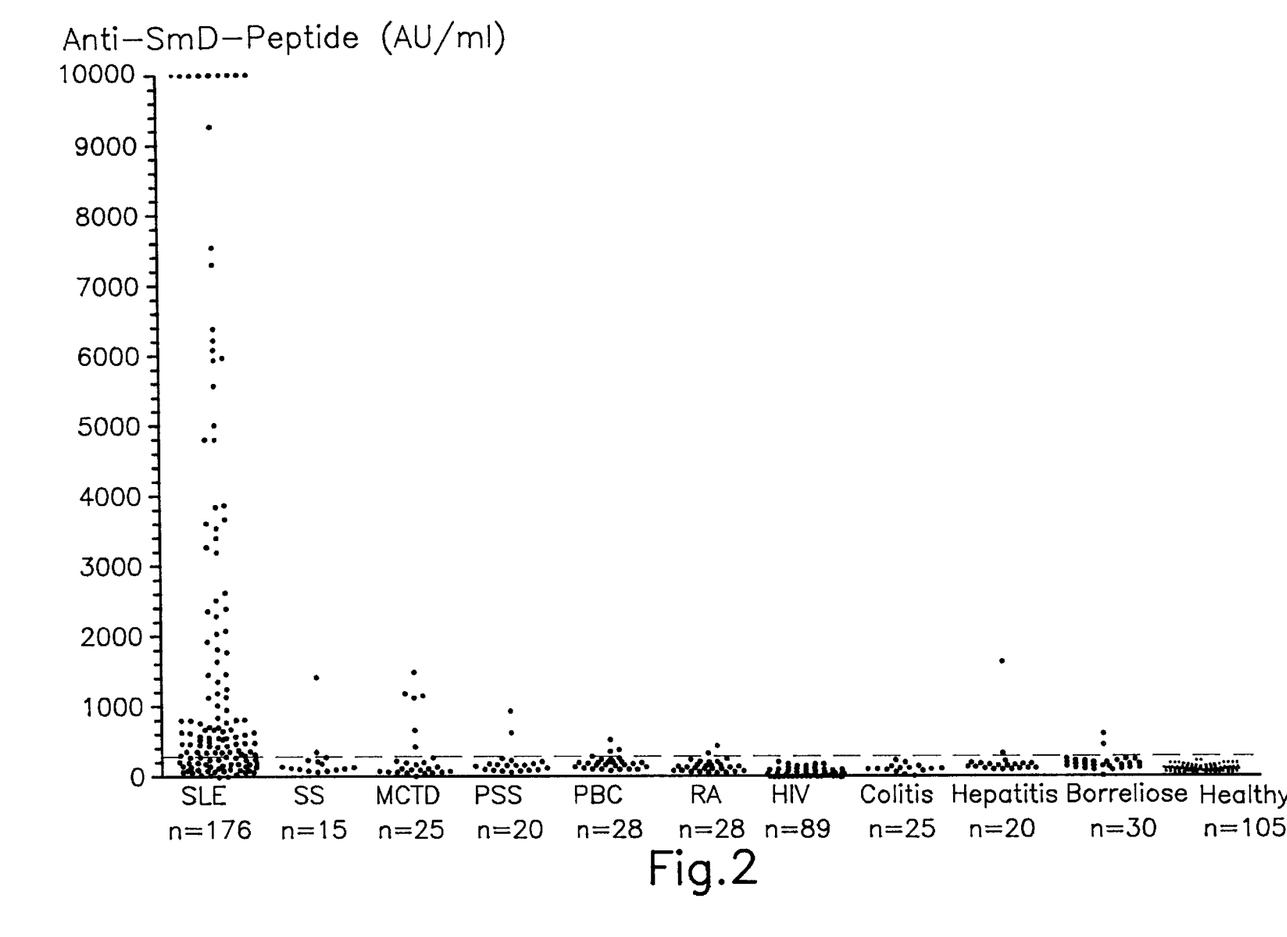
FIG. 2 is a diagram showing anti-SmD (83–119) antibodies in SLE patients and control groups.

67.3% of all investigated SLE sera, antibodies against the peptide 83–119 were detected. Thus, the ELISA is highly specific for the SLE. Individually, positive reactions occur also in the MCTD or in the RA, high concentrations however were nearly only achieved in connection with SLE (FIG. 2).

Figure 3:
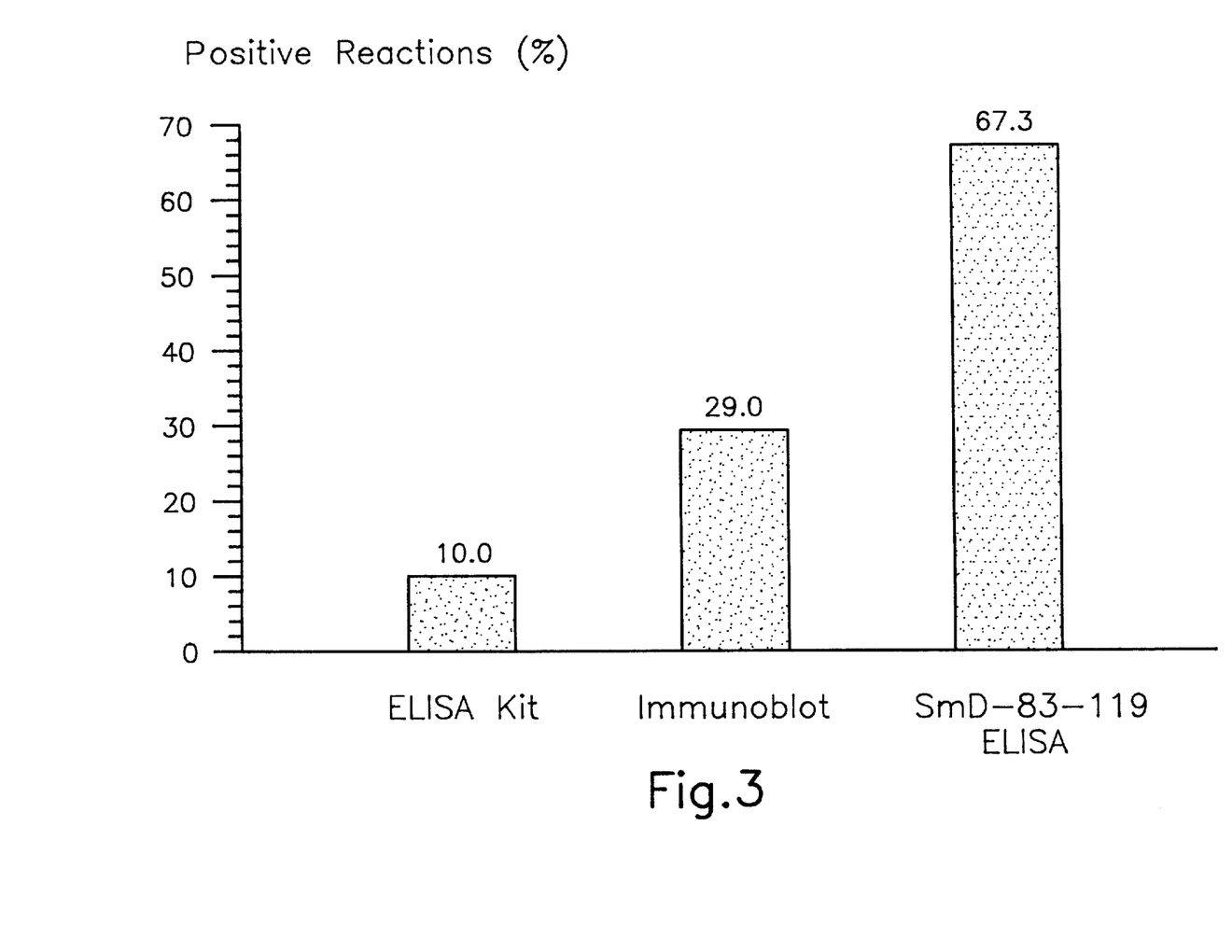
FIG. 3 is a block diagram showing a comparison of different methods during showing of presence of anti-Sm (d) antibodies.

Upon employment of a commercial anti-Sm-ELISA (Sm-Elias), the anti-Sm antibodies could be detected only in 10% of the sera (FIG. 3).

Figure 4:
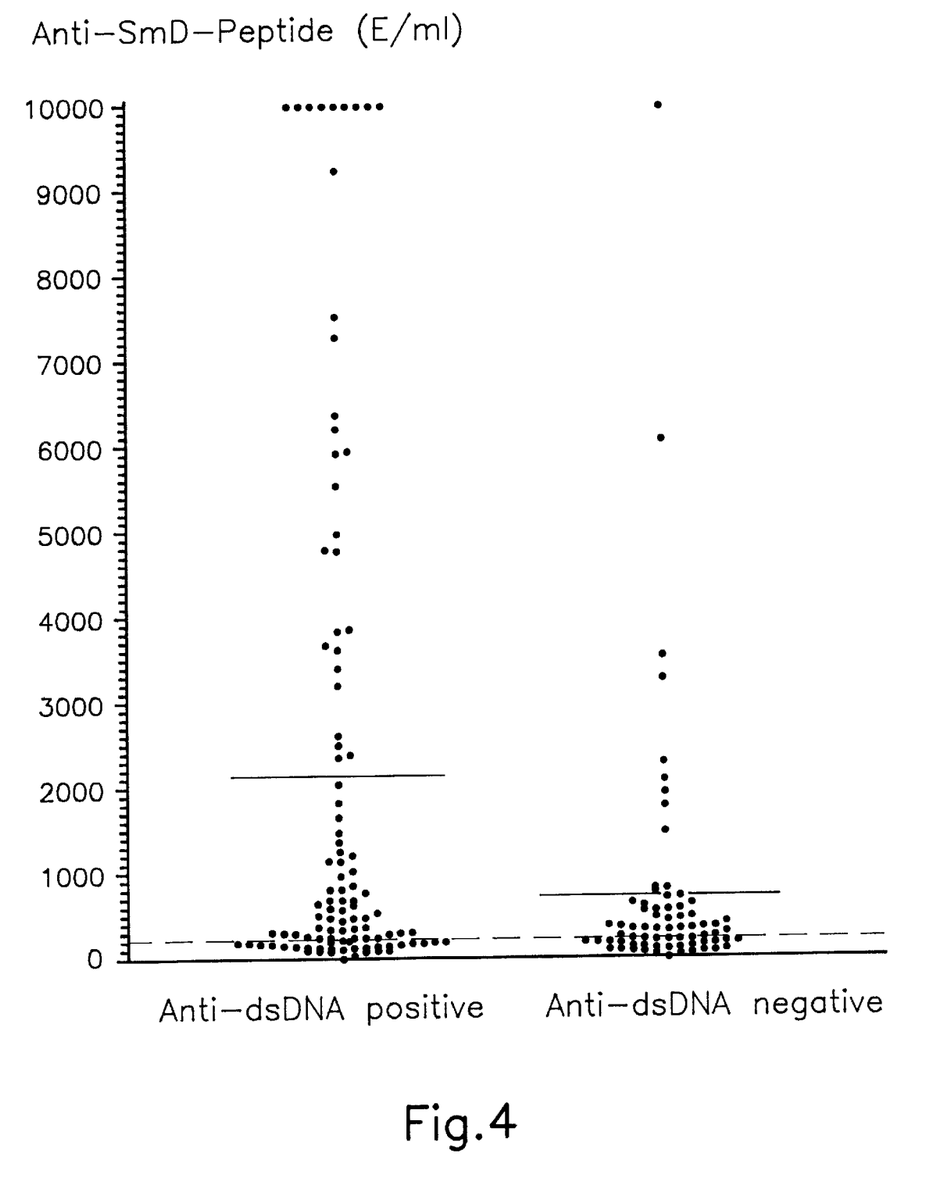
FIG. 4 is a diagram showing the relation between the anti-SmD (83–119) reactivities in the ELISA and the occurrence of anti-dsDNS in the immunofluorescence.
Figure 5:
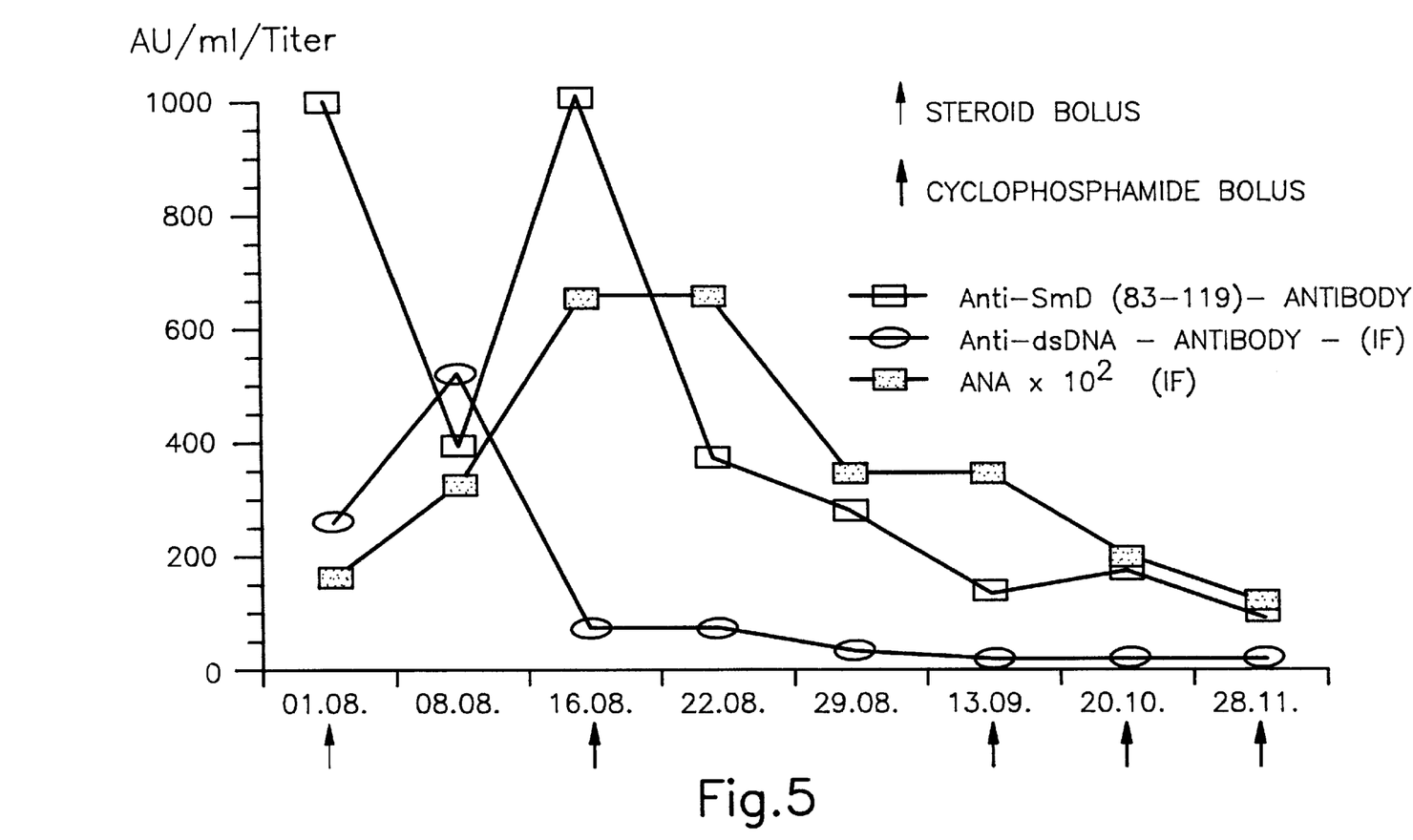
FIG. 5 is a diagram showing the change of the antibody reactivities against the peptide SmD (83–119) depending on the activity of the SLE.

If one compares SLE sera with negative anti-dsDNA antibodies with those with [translator's remark: positive] anti-double-stranded deoxyribonucleic acid (anti-dsDNA) antibodies, then the antibodies against the SmD peptide can be detected in significantly higher titers in the case of anti-ds-DNA antibody-positive patients (FIG. 4). The reactivity in the ELISA appear furthermore to be independent of the activity of the sickness. In order to test this observation, six patients were investigated over the course in time. FIG. 5 shows the course of a typical patient and the influence of the therapy on the titer of the autoantibodies. The anti-peptide antibodies were detectable in a patient, even though the anti-DsDNA antibodies were negative.

Assessments of the course can be performed relatively simple and quickly with the development of this new test with the peptide 83–119 disposed at the solid phase. Thus, the new tests represent a good alternative to the conventional expensive test.

EXAMPLE 3

Detecting of Autoantibodies against other Autoantigens

Figure 6:
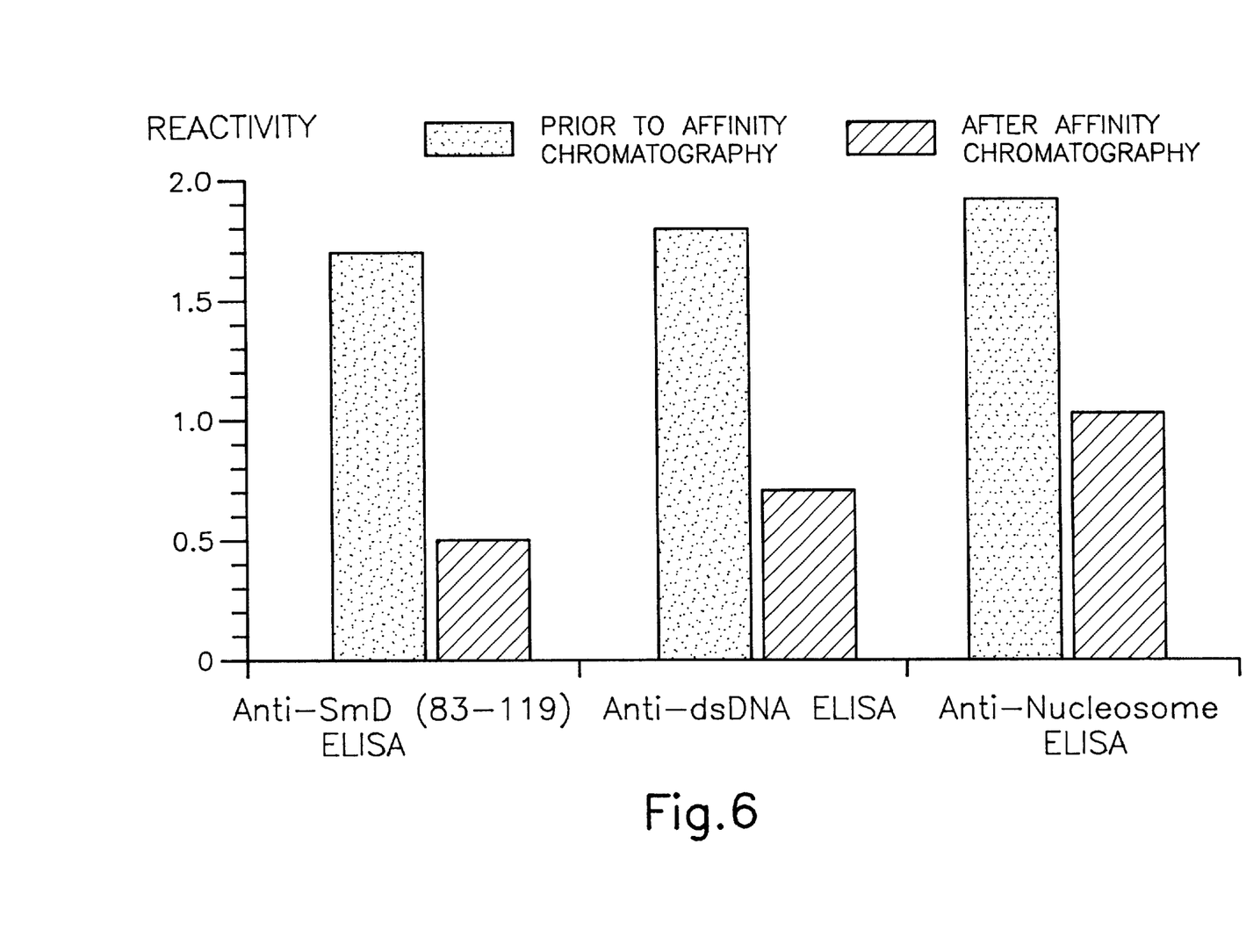
FIG. 6 is a block diagram showing the lowering of the reactivities of anti-SmD (83–119) antibodies, anti-dsDNA antibodies, and anti-nucleosome antibodies by affinity chromatography.

The frequency of the anti-peptide antibodies corresponds thus nearly to the presence of the anti-dsDNA antibodies. Recently, Reichlin and coworkers could show a cross reactivity of the anti-ds-DNA antibodies with the antibodies against the Sm-D and the A protein of the snRNP (M. A. Reichlin et al, J. Clin. Invest. 1994; 93: 443–449). Since only a small homology exists between the amino acids, the cause of the cross reaction was connected to a possible conformation epitope. In order to show a possible cross reactivity of the anti-SmD$_{(83-119)}$ antibodies with other autoantibodies, an affinity chromatography with the SmD$_{(83-119)}$ peptide, bound to Sepharose, was performed and the extinctions in the different ELISAs prior to and after eluation of the anti-peptide antibodies were measured (FIG. 6). A significant decrease occurred both in the anti-SmD peptide ELISA and in the ELISA for detecting anti-dsDNA antibodies and antibodies against nucleosomes. Consequently, cross reactions appeared to be present in these autoantigens.

We claim:

1. A peptide of the antigen Sm-D, consisting of from 35–45 amino acids, wherein said peptide forms a conformation epitope and binds autoantibodies from patients with systemic lupus erythematosus (SLE), wherein said peptide comprises an amino acid sequence selected from the group consisting of the following amino acid sequences:
   a) PKVKSKKREAVAGRGRGRGRGRGRGRGR GGPRR, SEQ ID No. 1,
   b) EPKVKSKKREAVAGRGRGRGRGRGRGRG RGGPRR, SEQ ID No. 2,
   c) VEPKVKSKKREAVAGRGRGRGRGRGRGR GRGGPRR, SEQ ID No. 3,
   d) DVEPKVKSKKREAVAGRGRGRGRGRGRG RGRGGPRR, SEQ ID No. 4,
   e) VDVEPKVKSKKREAVAGRGRGRGRGRGR GRGRGGPRR, SEQ ID No. 5,
   f) RVDVEPKVKSKKREAVAGRGRGRGRGRGR GRGRGGPRR, SEQ ID No. 6,
   g) IRVDVEPKVKSKKREAVAGRGRGRGRGRG RGRGRGGPRR, SEQ ID No. 7,
   h) TIRDDVEPKVKSKKREAVAGRGRGRGRGR GRGRGGPRR, SEQ ID No. 8,
   i) DTIRVDVEPKVKSKKREAVAGRGRGRGRGR GRGRGRGGPRR, SEQ ID No. 9,
   j) LDTIRVDVEPKVKSKKREAVAGRGRGRGRGR GRGRGRGGPRR, SEQ ID No. 10, and
   k) PLDTIRVDVEPKVKSKKREAVAGRGRGRGR GRGRGRGRGGPRR, SEQ ID No. 11.

2. An antigen composition comprising peptides of the antigen Sm-D, wherein said peptides consist of from 35–45 amino acids, wherein said peptides form a conformation epitope and bind autoantibodies from patients with systemic lupus erythematosus (SLE), wherein said peptides comprise an amino acid sequence selected from the group consisting of the following amino acid sequences:
   a) PKVKSKKREAVAGRGRGRGRGRGRGRGRG GPRR, SEQ ID No. 1,
   b) EPKVKSKKREAVAGRGRGRGRGRGRGRG RGGPRR, SEQ ID No. 2,
   c) VEPKVKSKKREAVAGRGRGRGRGRGRGRG RGGPRR, SEQ ID No. 3,
   d) DVEPKVKSKKREAVAGRGRGRGRGRGRGRG RGGPRR, SEQ ID No. 4,
   e) VDVEPKVKSKKREAVAGRGRGRGRGRGRGR GRGGPRR, SEQ ID No. 5,
   f) RVDVEPKVKSKKREAVAGRGRGRGRGRGRGR GRGGPRR, SEQ ID No. 6,
   g) IRVDVEPKVKSKKREAVAGRGRGRGRGRGRGR GRGGPRR, SEQ ID No. 7,
   h) TIRVDVEPKVKSKKREAVAGRGRGRGRGRGRGR GRGGPRR, SEQ ID No. 8,
   i) DTIRVDVEPKVKSKKREAVAGRGRGRGRGRG RGRGRGGPRR, SEQ ID No. 9,
   j) LDTIRVDVEPKVKSKKREAVAGRGRGRGRGRG RGRGRGGPRR, SEQ ID No. 10, and
   k) PLDTIRVDVEPKVKSKKREAVAGRGRGRGRGRG RGRGRGGPRR, SEQ ID No. 11.

3. An immunogenic composition comprising peptides of the antigen Sm-D, wherein said peptides consist of from 35–45 amino acids, wherein said peptides form a conformation epitope and bind autoantibodies from patients with systemic lupus erythematosus (SLE), wherein said peptides comprise an amino acid sequence selected from the group consisting of the following amino acid sequences:
   a) PKVKSKKREAVAGRGRGRGRGRGRGRGG PRR, SEQ ID No. 1,
   b) EPKVKSKKREAVAGRGRGRGRGRGRGRG RGGPRR, SEQ ID No. 2,
   c) VEPKVKSKKREAVAGRGRGRGRGRGRGRGR GGPRR, SEQ ID No. 3,
   d) DVEPKVKSKKREAVAGRGRGRGRGRGRGRG RGGPRR, SEQ ID No. 4,
   e) VDVEPKVKSKKREAVAGRGRGRGRGRGRGR GRGGPRR, SEQ ID No. 5,
   f) RVDVEPKVKSKKREAVAGRGRGRGRGRGRG RGRGGPRR, SEQ ID No. 6,
   g) IRVDVEPKVKSKKREAVAGRGRGRGR-GRGRG RGRGGPRR, SEQ ID No. 7,
   h) TIRVDVEPKVKSKKREAVAGRGRGRGRGRGR GRGRGGPRR, SEQ ID No. 8,
   i) DTIRVDVEPKVKSKKREAVAGRGRGRGRGRG RGRGRGGPRR, SEQ ID No. 9,
   j) LDTIRVDVEPKVKSKKREAVAGRGRGRGRGRG RGRGRGGPRR, SEQ ID No. 10, and
   k) PLDTIRVDVEPKVKSKKREAVAGRGRGRGRGRG RGRGRGRGGPRR, SEQ ID No. 11.

4. The immunogenic composition of claim 3, wherein the peptides induce the production of antibodies, wherein said antibodies are capable of recognizing autoantigens from patients with systemic lupus erythematosus (SLE), and wherein said peptides are formed as compounds in connection with a carrier molecule.

5. An immunogenic composition comprising peptides of the antigen Sm-D, wherein said peptides consist of from 35–45 amino acids, wherein said peptides form a conformation epitope and wherein the peptides induce the production of antibodies, wherein said antibodies are capable of recognizing autoantigens from patients with systemic lupus erythematosus (SLE), wherein said peptides are formed as compounds in connection with a carrier molecule, and wherein said peptides comprise an amino acid sequence selected from the group consisting of the following amino acid sequences:
   a) PKVKSKKREAVAGRGRGRGRGRGRGRGRGG PRR, SEQ ID No. 1,
   b) EPKVKSKKREAVAGRGRGRGRGRGRGRGRG RGGPRR, SEQ ID No. 2,
   c) VEPKVKSKKREAVAGRGRGRGRGRGRGRGR GRGGPRR, SEQ ID No. 3,
   d) DVEPKVKSKKREAVAGRGRGRGRGRGRGRGR GRGGPRR, SEQ ID No. 4,
   e) VDVEPKVKSKKREAVAGRGRGRGRGRGRGR GRGGPRR, SEQ ID No. 5, f) RVDVEPKVKSKKREAVAGRGRGRGRGRGRGR GRGRGGPRR, SEQ ID No. 6, g) IRVDVEPKVKSKKREAVAGRGRGRGRGRGR GRGRGGPRR, SEQ ID No. 7, h) TIRVDVEPKVKSKKREAVAGRGRGRGRGRGR GRGRGGPRR, SEQ ID No. 8, i) DTIRVDVEPKVKSKKREAVAGRGRGRGRG RGRGRGRGGPRR, SEQ ID No. 9, j) LDTIRVDVEPKVKSKKREAVAGRGRGRGRG RGRGRGRGGPRR, SEQ ID No. 10, and k) PLDTIRVDVEPKVKSKKREAVAGRGRGRGRG RGRGRGRGGPRR, SEQ ID No. 11.

6. The antigen composition according to claim 2, wherein the peptides comprise the amino acid sequence VEPKVKSKKREAVAGRGRGRGRGRGRGRGGPRR, SEQ ID No. 3, and wherein said peptides are capable of reacting with autoantibodies present in biological fluids of patients with SLE.

7. The immunogenic composition according to claim 3, wherein the peptides induce the production of antibodies, which antibodies are capable of recognizing autoantigens of patients with SLE.

8. The immunogenic composition according to claim 3, wherein said peptides are formed as compounds in connection with a carrier molecule.

9. The immunogenic composition according to claim 3, wherein the peptides comprise the amino acid sequence VEPKVKSKKREAVAGRGRGRGRGRGRGRGGPRR, SEQ ID No. 3, and wherein said peptides are capable of inducing a production of antibodies, wherein the antibodies are capable of recognizing autoantigens in biological fluids of patients with SLE.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
       (A) LENGTH: 35 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 1:

Pro Lys Val Lys Ser Lys Lys Arg Glu Ala Val Ala Gly Arg Gly Arg
1               5                   10                  15

Gly Arg Gly Arg Gly Arg Gly Arg Gly Arg Gly Arg Gly Arg Gly Gly
            20                  25                  30

Pro Arg Arg
        35

(2) INFORMATION FOR SEQ ID NO: 2:

(i) SEQUENCE CHARACTERISTICS:
       (A) LENGTH: 36 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 2:

Glu Pro Lys Val Lys Ser Lys Lys Arg Glu Ala Val Ala Gly Arg Gly
1               5                   10                  15

Arg Gly Arg Gly Arg Gly Arg Gly Arg Gly Arg Gly Arg Gly Arg Gly
            20                  25                  30

Gly Pro Arg Arg
        35

(2) INFORMATION FOR SEQ ID NO: 3:

(i) SEQUENCE CHARACTERISTICS:
       (A) LENGTH: 37 amino acids
       (B) TYPE: amino acid
       (C) STRANDEDNESS: single (D) TOPOLOGY: linear (ii) MOLECULE TYPE: peptide (xi) SEQUENCE DESCRIPTION: SEQ ID NO: 3:

```
Val Glu Pro Lys Val Lys Ser Lys Lys Arg Glu Ala Val Ala Gly Arg
1               5                   10                  15
Gly Arg Gly Arg Gly Arg Gly Arg Gly Arg Gly Arg Gly Arg Gly Arg
                20                  25                  30
Gly Gly Pro Arg Arg
        35
```

(2) INFORMATION FOR SEQ ID NO: 4:

(i) SEQUENCE CHARACTERISTICS:
    (A) LENGTH: 38 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 4:

```
Asp Val Glu Pro Lys Val Lys Ser Lys Lys Arg Glu Ala Val Ala Gly
1               5                   10                  15
Arg Gly Arg Gly Arg Gly Arg Gly Arg Gly Arg Gly Arg Gly Arg Gly
                20                  25                  30
Arg Gly Gly Pro Arg Arg
        35
```

(2) INFORMATION FOR SEQ ID NO: 5:

(i) SEQUENCE CHARACTERISTICS:
    (A) LENGTH: 39 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 5:

```
Val Asp Val Glu Pro Lys Val Lys Ser Lys Lys Arg Glu Ala Val Ala
1               5                   10                  15
Gly Arg Gly Arg Gly Arg Gly Arg Gly Arg Gly Arg Gly Arg Gly Arg
                20                  25                  30
Gly Arg Gly Gly Pro Arg Arg
        35
```

(2) INFORMATION FOR SEQ ID NO: 6:

(i) SEQUENCE CHARACTERISTICS:
    (A) LENGTH: 40 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 6:

```
Arg Val Asp Val Glu Pro Lys Val Lys Ser Lys Lys Arg Glu Ala Val
1               5                   10                  15
Ala Gly Arg Gly Arg Gly Arg Gly Arg Gly Arg Gly Arg Gly Arg Gly
                20                  25                  30
Arg Gly Arg Gly Gly Pro Arg Arg
        35              40
```

(2) INFORMATION FOR SEQ ID NO: 7:

(i) SEQUENCE CHARACTERISTICS:
        (A) LENGTH: 41 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 7:

```
Ile Arg Val Asp Val Glu Pro Lys Val Lys Ser Lys Lys Arg Glu Ala
1               5                   10                  15

Val Ala Gly Arg Gly Arg Gly Arg Gly Arg Gly Arg Gly Arg
            20                  25                  30

Gly Arg Gly Arg Gly Gly Pro Arg Arg
        35                  40
```

(2) INFORMATION FOR SEQ ID NO: 8:

(i) SEQUENCE CHARACTERISTICS:
        (A) LENGTH: 42 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 8:

```
Thr Ile Arg Val Asp Val Glu Pro Lys Val Lys Ser Lys Lys Arg Glu
1               5                   10                  15

Ala Val Ala Gly Arg Gly Arg Gly Arg Gly Arg Gly Arg Gly Arg Gly
            20                  25                  30

Arg Gly Arg Gly Arg Gly Gly Pro Arg Arg
        35                  40
```

(2) INFORMATION FOR SEQ ID NO: 9:

(i) SEQUENCE CHARACTERISTICS:
        (A) LENGTH: 43 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 9:

```
Asp Thr Ile Arg Val Asp Val Glu Pro Lys Val Lys Ser Lys Lys Arg
1               5                   10                  15

Glu Ala Val Ala Gly Arg Gly Arg Gly Arg Gly Arg Gly Arg Gly Arg
            20                  25                  30

Gly Arg Gly Arg Gly Arg Gly Gly Pro Arg Arg
        35                  40
```

(2) INFORMATION FOR SEQ ID NO: 10:

(i) SEQUENCE CHARACTERISTICS:
        (A) LENGTH: 44 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 10:

```
Leu Asp Thr Ile Arg Val Asp Val Glu Pro Lys Val Lys Ser Lys Lys
 1               5                  10                  15

Arg Glu Ala Val Ala Gly Arg Gly Arg Gly Arg Gly Arg Gly
         20                  25                  30

Arg Gly Arg Gly Arg Gly Arg Gly Gly Pro Arg Arg
         35                  40
```

(2) INFORMATION FOR SEQ ID NO: 11:

(i) SEQUENCE CHARACTERISTICS:
        (A) LENGTH: 45 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 11:

```
Pro Leu Asp Thr Ile Arg Val Asp Val Glu Pro Lys Val Lys Ser Lys
 1               5                  10                  15

Lys Arg Glu Ala Val Ala Gly Arg Gly Arg Gly Arg Gly Arg Gly Arg
         20                  25                  30

Gly Arg Gly Arg Gly Arg Gly Arg Gly Gly Pro Arg Arg
         35                  40                  45
```

(2) INFORMATION FOR SEQ ID NO: 12:

(i) SEQUENCE CHARACTERISTICS:
        (A) LENGTH: 17 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 12:

```
Val Glu Pro Lys Val Lys Ser Lys Lys Arg Glu Ala Val Ala Gly Arg
 1               5                  10                  15

Gly
```

(2) INFORMATION FOR SEQ ID NO: 13:

(i) SEQUENCE CHARACTERISTICS:
        (A) LENGTH: 25 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 13:

```
Val Ala Gly Arg Gly Arg Gly Arg Gly Arg Gly Arg Gly Arg Gly Arg
 1               5                  10                  15

Gly Arg Gly Arg Gly Gly Pro Arg Arg
         20                  25
```

(2) INFORMATION FOR SEQ ID NO: 14:

(i) SEQUENCE CHARACTERISTICS:
        (A) LENGTH: 15 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO: 14:

```
Gly Arg Gly Arg Gly Arg Gly Arg Gly Arg Gly Gly Pro Arg Arg
1               5                   10              15
```